(12) United States Patent
Anderson

(10) Patent No.: US 8,790,345 B2
(45) Date of Patent: Jul. 29, 2014

(54) TITANIUM ALLOY WITH OXIDIZED ZIRCONIUM FOR A PROSTHETIC IMPLANT

(75) Inventor: Jeffrey P. Anderson, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 1648 days.

(21) Appl. No.: 11/842,584

(22) Filed: Aug. 21, 2007

(65) Prior Publication Data

US 2009/0054985 A1 Feb. 26, 2009

(51) Int. Cl.
*A61B 17/56* (2006.01)
(52) U.S. Cl.
USPC .......................................................... 606/76
(58) Field of Classification Search
USPC .......................................................... 606/76
See application file for complete search history.

(56) References Cited

U.S. PATENT DOCUMENTS

| | | | |
|---|---|---|---|
| 2,987,352 A | 6/1961 | Watson | |
| 3,677,795 A | 7/1972 | Bokros et al. | |
| 4,145,764 A | 3/1979 | Suzuki et al. | |
| 4,487,808 A | 12/1984 | Lambert | |
| 4,671,824 A | 6/1987 | Haygarth | |
| 4,704,126 A * | 11/1987 | Baswell et al. | 623/10 |
| 5,037,438 A * | 8/1991 | Davidson | 623/22.15 |
| 5,258,022 A | 11/1993 | Davidson | |
| 5,316,594 A | 5/1994 | Kemp | |
| 5,324,009 A | 6/1994 | Kemp | |
| 5,383,934 A | 1/1995 | Armini et al. | |
| 5,399,207 A | 3/1995 | Kemp | |
| 5,409,703 A | 4/1995 | McAnalley et al. | |
| 5,464,440 A | 11/1995 | Johansson | |
| 5,509,899 A | 4/1996 | Fan et al. | |
| 5,612,052 A | 3/1997 | Shalaby | |
| 5,714,159 A | 2/1998 | Shalaby | |
| 5,980,974 A | 11/1999 | Armini et al. | |
| 6,080,488 A | 6/2000 | Hostettler et al. | |
| 6,110,483 A | 8/2000 | Whitbourne et al. | |
| 6,176,849 B1 | 1/2001 | Yang et al. | |
| 6,410,044 B1 | 6/2002 | Chudzik et al. | |
| 6,413,539 B1 | 7/2002 | Shalaby | |
| 6,544,472 B1 | 4/2003 | Compton | |
| 6,585,772 B2 * | 7/2003 | Hunter et al. | 623/23.54 |
| 6,726,725 B2 | 4/2004 | Hunter et al. | |

(Continued)

FOREIGN PATENT DOCUMENTS

| | | |
|---|---|---|
| EP | 0608997 A1 | 8/1994 |
| EP | 1679088 A2 | 12/2006 |
| EP | 1806155 A2 | 7/2007 |
| WO | WO2007/121242 A2 | 10/2007 |

OTHER PUBLICATIONS

International Search Report mailed Aug. 16, 2010 in International Application No. PCT/US2009/050709.

(Continued)

*Primary Examiner* — Christian Sevilla
(74) *Attorney, Agent, or Firm* — Schwegman Lundberg & Woessner, P.A.

(57) ABSTRACT

A prosthetic device having a generally fixed member formed from a low friction material such as ultra-high molecular weight polyethylene and an articulating titanium member, which includes an articular bearing surface. The articular surface is a zirconium oxide layer formed by applying a coating of zirconium onto the titanium member and heating this in an oxygen-containing environment. This causes the zirconium to oxidize and further causes the zirconium to migrate into the titanium member forming a titanium zirconium diffusion layer, which prevents delamination.

20 Claims, 1 Drawing Sheet

(56) References Cited

U.S. PATENT DOCUMENTS

| | | | |
|---|---|---|---|
| 7,070,623 B2 | 7/2006 | Hunter et al. | |
| 2002/0072807 A1 | 6/2002 | Nawa et al. | |
| 2003/0036794 A1 | 2/2003 | Ragheb et al. | |
| 2003/0220699 A1* | 11/2003 | Hunter et al. | 623/23.54 |
| 2006/0233944 A1* | 10/2006 | Popoola et al. | 427/2.24 |
| 2006/0259150 A1 | 11/2006 | Hunter et al. | |
| 2006/0276900 A1* | 12/2006 | Carpenter | 623/17.15 |
| 2007/0078521 A1 | 4/2007 | Overholser et al. | |

OTHER PUBLICATIONS

Article "Ceramic Formation on Metallic Surfaces (Ceramization) for Medical Application," J. Rieu, Clinical Materials 12 (1993) pp. 227-235 RIEU.

Article "Microstructure and Erosion Resistance of Vacuum-plasma-sprayed Co-Ni-Cr-Al-Y/Al2O3 Composite Coatings," B. Gudmundsson et al., Materials Science and Engineering, A108 (1989), pp. 87-95 Gudmundsson.

* cited by examiner

TITANIUM ALLOY WITH OXIDIZED ZIRCONIUM FOR A PROSTHETIC IMPLANT

FIELD OF THE INVENTION

This invention relates to implantable prosthetic devices and, more particularly, to such devices with a reduced friction coating.

BACKGROUND OF THE INVENTION

Implantable prosthetic devices such as artificial hips, knees, ankles, elbows, and shoulders, as well as spinal cord implants, must provide for movement or articulation of multiple parts or members. Generally, one member moves relative to a second member that is fixed and formed from wear-resistant plastic, for example, ultra-high molecular weight polyethylene.

The repeated movement of the respective members of the prosthetic implant will wear the softer plastic causing deterioration. It is generally an object of these prosthetic devices to minimize this wear to the extent possible. This involves a trade-off of relative characteristics. Ceramic surfaces provide reduced wear, but are more brittle. Metals possess the requisite strength but cause additional wear.

Certain alloys provide less wear; for example cobalt-chromium-molybdenum alloys provide very low wear. However, there is concern about metal ion release from certain of these alloys with the possibility of causing an allergic reaction. Titanium or titanium alloy load bearing members are extremely strong, but can cause more wear than, for example, a ceramic or cobalt-chromium-molybdenum alloy member.

SUMMARY OF THE INVENTION

The present invention is premised on the realization that the wear between two members of a prosthetic device can be reduced wherein one of the members is formed from titanium that has an outer peripheral articular surface coated with zirconium oxide.

Preferably the coating is applied by first depositing a layer of zirconium onto the articular surface of the titanium member, and subsequently heating the zirconium in an oxidizing environment to form zirconium oxide. The temperature is selected so that the outer surface of the zirconium oxidizes while the inner portion of the deposited zirconium diffuses into the titanium surface, forming a strong bond that will not delaminate.

The objects and advantages of the present invention will be further appreciated in light of the following detailed description and drawings.

DETAILED DESCRIPTION

Figure 1:
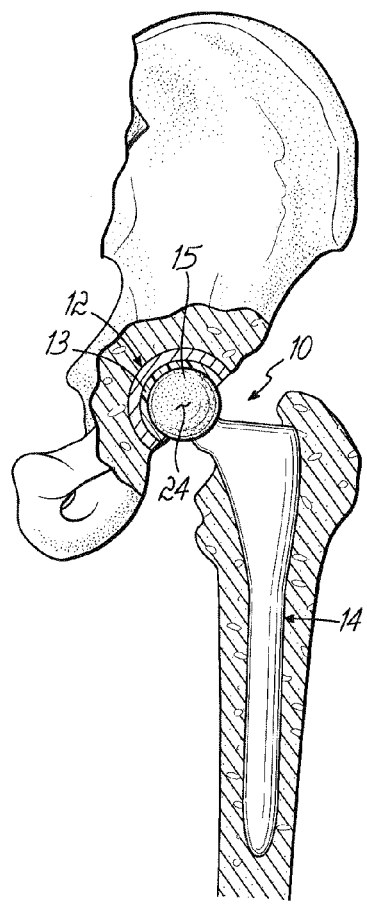
FIG. 1 is a cross-sectional view broken away of an exemplary prosthetic implant.

As shown in FIG. 1, an implanted prosthetic device, in this drawing shown as a hip replacement 10, includes a fixed bearing member 12, which has a cup-shaped bearing surface 13 and a metal load bearing member 14 which is fixed to a patient's leg. Metal load bearing member 14 has a head 15, which engages fixed bearing member 12. Although the figure shows a hip implant, the bearing member 12 and metal member 14 are exemplary of any implant that has a bearing member 12 and a moving metal member 14. These include implanted knee joints, ankle joints, elbow joints, shoulder joints and spinal implants.

The fixed bearing member 12, which is typical of bearing members used in implantable devices, is formed from a low-friction material, typically a polymer. This can be, for example, polyethylene and, particularly, ultra-high molecular weight polyethylene.

Again, with reference to FIG. 1 the load bearing member 14 of the implant 10 is formed from titanium. Although it can be titanium metal, a titanium alloy is preferred. Any biocompatible titanium alloy typically employed in prosthetic devices can be used in the present invention. One typical titanium alloy is Ti-6% Al-4% V. Both elemental titanium and titanium alloy will simply be referred to as titanium.

Figure 2:
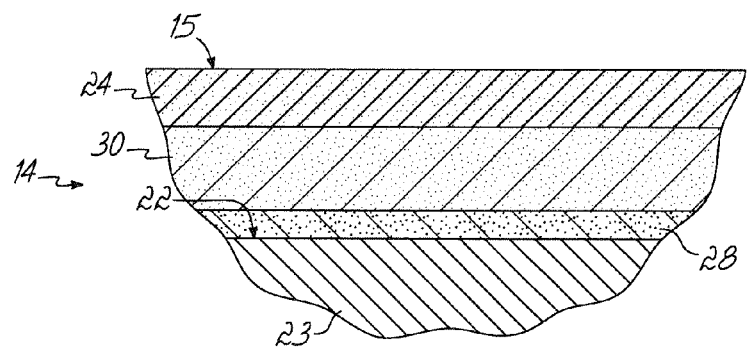
FIG. 2 is a diagrammatic cross-sectional view broken away of a portion of an exemplary prosthetic implant.

The head 15 of titanium load bearing member 14 has a peripheral articular surface 22, which is coated with a layer of zirconium oxide 24. FIG. 2 represents the peripheral surface 22 of head 15. As shown, this is a multilayered surface which starts with the unreacted titanium metal portion 23 which forms the member 14. Outwardly from metal portion 23 is a diffusion layer 28 of zirconium and titanium. Again, outwardly from layer 28 is a layer 30 of unreacted zirconium, followed by the outermost zirconium oxide layer 24. Preferably, the zirconium oxide layer 24 will be at least about 1 micron thick and preferably up to about 5 microns thick to allow for polishing to remove surface imperfections. The diffusion layer is preferably around 1 micron thick.

The zirconium oxide coating is applied to the peripheral articular surface 22 of titanium member 14 which is formed by, for example, casting or the like. Surface 22 of head 15 is polished to minimize surface imperfections and is then coated with a layer of zirconium or a zirconium alloy. The zirconium alloy can be any alloy that is predominately zirconium. Generally these will have at least about 80 per cent zirconium. Preferably, 100 per cent zirconium is utilized. Again, elemental zirconium and zirconium alloy are generically referred to as zirconium.

The zirconium layer can be deposited on surface 22 by physical vapor deposition, chemical vapor deposition, ion beam assisted vapor deposition, electro-chemical plating and the like. The deposited zirconium layer should be from about 1 micron and, preferably, at least about 2 microns to about 10 microns with about 7 microns preferred. Generally, the deposition method limits the thickness due to the possibility of forming fractures and stresses, which increases with thickness.

The outer surface of the deposited zirconium layer is oxidized to form zirconium oxide. Although not limited to any particular method of oxidization, preferably the head 15 coated with zirconium is heated in an oxygen-containing atmosphere, such as air, steam or oxygen enriched air, at a temperature effective to cause oxidation. The temperature will also be effective to cause the zirconium to diffuse into the titanium layer to form the diffusion layer 28.

To accomplish this, head 15 should be heated to about 450° C. to about 1000° C., preferably about 590° C., for about 1 to about 14 hours, and preferably about 1 to about 7 hours in air. The lower temperature limit is a practical limitation. In order to achieve a 1-micron diffusion layer within 10 hours, the temperature needs to be about 460° C. The reaction rate increases with the temperature. Above 1000° C. a less stable zirconium oxide forms, which should be avoided. The particular oxidation reaction time should be chosen to obtain the desired thickness of zirconium oxide at the selected reaction temperature. Reacting the zirconium in air at 500° C. for 6 hours provides a 2-micron zirconium oxide layer.

This heating forms the outer surface of zirconium oxide, which extends below the surface about 1 to 5 microns, followed by the layer of unreacted zirconium 30 and the diffusion layer 28 of zirconium titanium. This diffusion layer 28 provides a strong bond between the titanium and the zirconium.

Finally, the zirconium oxide layer 24 is polished and the metal member 14 is ready to be implanted.

Any heat treatment of the titanium member 14 that is required for any other processing should be done prior to the formation of the zirconium oxide to prevent fracture of the zirconium oxide layer. For example, if the titanium member is coated with a porous coating at an elevated temperature, this should be done prior to deposition of the zirconium. The porous surface is then subsequently masked to avoid being coated with the zirconium.

This process will be further appreciated in light of the following detailed example.

EXAMPLE

A substrate of Ti-6% Al-4% V (weight percentages) was polished on one face to a roughness of less than 2 µin (Ra— average surface roughness).

A layer of Zr of thickness approximately 7 µm was deposited on the polished substrate surface by arc-evaporated physical vapor deposition, in which an electrical arc was established on the surface of a Zr target. The evaporated Zr ions were extracted to the Ti-alloy substrate (through an applied bias voltage) and deposited on the polished surface.

The specimen was heated in an inert argon atmosphere to 549° C. At that point the argon was replaced with flowing air, and heating continued to 582° C. The specimen was held at 582° C. for 4 hours and then cooled rapidly in argon to room temperature.

The now-oxidized specimen was sectioned and examined.

The chemical variations of Zr, O, Ti, Al and V were measured in the processed specimen. The chemical profile of the oxidized specimen suggests a zirconium-oxidized layer (most likely $ZrO_2$) about 1-1.5 µm thick, a layer of substantially pure Zr about 2-2.5 µm thick, an interdiffusion zone (about 1-1.5 µm thick) between the Zr layer and the Ti alloy substrate, and the Ti alloy substrate. This example illustrates the formation of the oxidized zirconium surface and the interdiffusion zone between the Zr and the Ti alloy substrate.

Utilizing the zirconium oxide-treated titanium surface of the present invention significantly reduces wear at the polyethylene surface and, thus, debris formation. This will reduce the likelihood of early aseptic loosening of the implant device caused by bone resorption triggered by polyethylene debris. Further, the zirconium titanium diffusion layer prevents delamination, chipping or cracking. Thus, the present invention improves the life of the implanted device.

This has been a description of the present invention along with the preferred method of practicing the present invention, however the invention itself should only be defined by the appended claims.

What is claimed is:

1. A method of forming a prosthetic implant wherein said implant comprises a first titanium articulating member having a first bearing surface and a second articulating member having a second bearing surface forming an articulable joint with said first bearing surface, said method comprising:
   depositing a coating of zirconium on at least a portion of said first bearing surface;
   heating said coating in an inert atmosphere; and
   heating said coating in the presence of oxygen, after heating said coating in an inert atmosphere;
   wherein the method results in an outer zirconium oxide layer, an inner titanium-zirconium diffusion layer, and an intermediate layer consisting essentially of zirconium, between the outer zirconium oxide layer and the inner titanium-zirconium diffusion layer, such that the inner titanium-zirconium diffusion layer prevents delamination.

2. The method of claim 1, wherein said coating of zirconium is about 2 microns to about 10 microns.

3. The method of claim 1, wherein said step of heating said coating in an inert atmosphere comprises heating said coating to a first temperature of at least about 450°C.

4. The method of claim 3, wherein said step of heating said coating in the presence of oxygen comprises heating said coating to a second temperature between about 540° C. and about 1000° C., and wherein said heating in the presence of oxygen is conducted for a period of between about 1 to about 14 hours.

5. The method of claim 1, wherein said first titanium articulating member is formed from a titanium-aluminum-vanadium alloy.

6. A method of preparing a wear-resistant bearing surface on a prosthetic implant, the prosthetic implant comprising a titanium surface or a titanium alloy surface, the method comprising:
   depositing onto said titanium or titanium alloy surface a coating of zirconium;
   heating said coating on said titanium or titanium alloy surface in an inert atmosphere; and
   heating said coating on said titanium or titanium alloy surface in the presence of oxygen, after heating said coating on said titanium or titanium alloy surface in an inert atmosphere;
   said method effective to cause an outer portion of said coating to form a zirconium oxide layer, an inner portion of said coating to diffuse unoxidized zirconium into said titanium or titanium alloy surface, and an intermediate portion of said coating, consisting essentially of zirconium, to remain unoxidized throughout said step of heating in the presence of oxygen, said method effective to prevent delamination.

7. The method of claim 6, further comprising, after said step of heating in the presence of oxygen, cooling the coated titanium or titanium alloy surface in an inert atmosphere.

8. The method of claim 1, wherein the outer zirconium oxide layer is at least about 1 micron thick.

9. The method of claim 1, wherein the outer zirconium oxide layer is up to about 5 microns thick.

10. The method of claim 1, wherein the inner titanium-zirconium diffusion layer is about 1 micron thick.

11. The method of claim 1, wherein the intermediate layer consisting essentially of zirconium is between about 2 microns to 2.5 microns thick.

12. The method of claim 4, wherein said second temperature is about 590° C., and wherein said step of heating in the presence of oxygen is conducted for a period of about 1 to about 7 hours.

13. The method of claim 4, wherein said second temperature is greater than said first temperature.

14. The method of claim 13, wherein said coating is held at said first temperature for a period of time, before it is heated to said second temperature.

15. The method of claim 1, further comprising, after said step of heating in the presence of oxygen, cooling said bearing surface in an inert atmosphere.

16. A method of preparing a zirconium-oxide surface on a prosthetic implant substrate, the prosthetic implant substrate comprising a titanium substrate surface or a titanium alloy substrate surface comprising:
   depositing onto said substrate surface a coating of zirconium;
   pre-heating the coated substrate surface to a first temperature in an inert atmosphere;
   exposing the coated substrate surface to oxygen; and
   heating the coated substrate surface to a second temperature for a period of time in the presence of said oxygen, said heating step effective to form an outer zirconium oxide layer that will not delaminate.

17. The method of claim 16, wherein said heating step is effective to form an inner titanium-zirconium diffusion layer, adjacent to the substrate surface, wherein the zirconium of the diffusion layer is unoxidized.

18. The method of claim 16, wherein said heating step is effective to form an intermediate layer, between said inner layer and diffusion layer, said intermediate layer consisting essentially of unoxidized zirconium.

19. The method of claim 16, further comprising, after said heating step, cooling the coated substrate in an inert atmosphere.

20. The method of claim 16, wherein said second temperature is greater than said first temperature.

* * * * *